(12) United States Patent
Isner et al.

(10) Patent No.: US 6,569,428 B1
(45) Date of Patent: May 27, 2003

(54) PHARMACEUTICAL PRODUCTS COMPRISING ENDOTHELIAL CELL PRECURSORS

(75) Inventors: Jeffrey M. Isner, Weston, MA (US); Takayuki Asahara, Arlington, MA (US)

(73) Assignee: St. Elizabeth's Medical Center of Boston, Inc., Boston, MA (US)

( * ) Notice: Subject to any disclaimer, the term of this patent is extended or adjusted under 35 U.S.C. 154(b) by 0 days.

(21) Appl. No.: 09/228,020

(22) Filed: Jan. 11, 1999

Related U.S. Application Data (62) Division of application No. 08/744,882, filed on Nov. 8, 1996, now Pat. No. 5,980,887.

(51) Int. Cl.[7] .................. A61K 35/12; A61K 48/00; A61K 38/18; A61K 38/19
(52) U.S. Cl. .................. 424/93.7; 514/44; 536/23.1; 536/23.5; 536/23.6; 536/23.7; 435/325
(58) Field of Search .................. 435/325; 424/93.7; 536/23.1, 23.5, 23.6, 23.7; 514/44

(56) References Cited

U.S. PATENT DOCUMENTS 5,874,301 A * 2/1999 Keller et al.
5,980,887 A * 11/1999 Isner et al.

FOREIGN PATENT DOCUMENTS

| WO | WO 89/03875 | 5/1989 |
| WO | WO 92/07573 | 5/1992 |
| WO | WO 93/13807 | 7/1993 |
| WO | WO 96/06933 | 3/1996 |
| WO | WO 97/12519 | 4/1997 |
| WO | WO 97/30083 | 8/1997 |

OTHER PUBLICATIONS

Miller, N et al. FASEB Journal. 9:190–199, Feb. 1995.*
Deonarain, MP. Exp. Opin. Ther. Patents. 8(1):53–69, 1998.*
Verma, IM et al. Nature. 389:239–242, Sep. 1997.*
Crystal, RG. Science. 270:404–410, Oct. 1995.*
1. Iwaguro et al. Circulation 105:732–738 (2002).*
2. Kalka et al. Circ. Res 86:1198–1202 (2000).*
3. Freedman et al. J. Mol. Cell Cardiol 33:379–393 (2001).*
C. Fennie et al. Blood 86: 4454–4467 (1995).
H. Schnurch et al. Development 119: 957–968 (1993).
T. P. Yamaguchi et al. Development 118: 489–498 (1993).
Asahara, et al., Science 275: 964–967 (1997).
Folkman and Shing, *J. Biol. Chem.* 267 (16), 10931–10934 (1992).
Baffour, et al., *J Vasc Surg*, 16:181–91 (1992)).
Takeshita, et al., *Circulation*, 90:228–234 (1994).
Takeshita, et al., *Laboratory Investigation*, 75:487–502 (1996).
Tsurumi et al., *Circulation*, vol. 94, No. 12, pp. 3281–3290 (1996).
Yanagisawa–Miwa, et al., *Science*, 257:1401–1403 (1992).
Pu, et al., *J Surg Res*, 54:575–83 (1993).
Isner, et al., *Lancet*, 348:370 (1996)).
Takeshita, et al., *J Clin Invest*, 93:662–70 (1994)).

\* cited by examiner

*Primary Examiner*—Phillip Gambel
(74) *Attorney, Agent, or Firm*—David G. Conlin; Dianne M. Rees; Edwards & Angell, LLP (57) ABSTRACT

Pharmaceutical products are provided comprising EC progenitors for use in methods for regulating angiogenesis, i.e., for enhancing or inhibiting blood vessel formation, in a selected patient and in some preferred embodiments for targeting an angiogenesis modulator to specific locations. For example, the EC progenitors can be used to enhance angiogenesis or to deliver an angiogenesis modulator, e.g., anti- or pro-angiogenic agents, respectively to sites of pathologic or utilitarian angiogenesis. Additionally, in another embodiment, EC progenitors can be used to induce reendothelialization of an injured blood vessel, and thus reduce restenosis by indirectly inhibiting smooth muscle cell proliferation.

24 Claims, 6 Drawing Sheets

```
SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:1:

AAGACATTTT CGGGCTCACG CTGCGCACCC                                           30

(2) INFORMATION FOR SEQ ID NO:2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:2:

TGGGGTAGGC ACTTTAGTAG TTCTCCTAAC                                           30
```

PHARMACEUTICAL PRODUCTS COMPRISING ENDOTHELIAL CELL PRECURSORS

This application is a divisional of U.S. Ser. No. 08/744,882 filed Nov. 8, 1996, now U.S. Pat. No. 5,980,887.

BACKGROUND OF THE INVENTION

Blood vessels are the means by which oxygen and nutrients are supplied to living tissues and waste products removed from living tissue. Angiogenesis is the process by which new blood vessels are formed, as reviewed, for example, by Folkman and Shing, J. Biol. Chem. 267 (16), 10931–10934 (1992). Thus angiogenesis is a critical process. It is essential in reproduction, development and wound repair. However, inappropriate angiogenesis can have severe consequences. For example, it is only after many solid tumors are vascularized as a result of angiogenesis that the tumors begin to grow rapidly and metastasize. Because angiogenesis is so critical to these functions, it must be carefully regulated in order to maintain health. The angiogenesis process is believed to begin with the degradation of the basement membrane by proteases secreted from endothelial cells (EC) activated by mitogens such as vascular endothelial growth factor (VEGF) and basic fibroblast growth factor (bFGF). The cells migrate and proliferate, leading to the formation of solid endothelial cell sprouts into the stromal space, then, vascular loops are formed and capillary tubes develop with formation of tight junctions and deposition of new basement membrane.

In the adults, the proliferation rate of endothelial cells is typically low compared to other cell types in the body. The turnover time of these cells can exceed one thousand days. Physiological exceptions in which angiogenesis results in rapid proliferation occurs under tight regulation are found in the female reproduction system and during wound healing.

The rate of angiogenesis involves a change in the local equilibrium between positive and negative regulators of the growth of microvessels. Abnormal angiogenesis occurs when the body loses its control of angiogenesis, resulting in either excessive or insufficient blood vessel growth. For instance, conditions such as ulcers, strokes, and heart attacks may result from the absence of angiogenesis normally required for natural healing. On the contrary, excessive blood vessel proliferation may favor tumor growth and spreading, blindness, psoriasis and rheumatoid arthritis.

The therapeutic implications of angiogenic growth factors were first described by Folkman and colleagues over two decades ago (Folkman, *N. Engl. J. Med.*, 285:1182–1186 (1971)). Thus, there are instances where a greater degree of angiogenesis is desirable—wound and ulcer healing. Recent investigations have established the feasibility of using recombinant angiogenic growth factors, such as fibroblast growth factor (FGF) family (Yanagisawa-Miwa, et al., *Science*, 257:1401–1403 (1992) and Baffour, et al., *J Vasc Surg*, 16:181–91 (1992)), endothelial cell growth factor (ECGF)(Pu, et al., *J Surg Res*, 54:575–83 (1993)), and more recently, vascular endothelial growth factor (VEGF) to expedite and/or augment collateral artery development in animal models of myocardial and hindlimb ischemia (Takeshita, et al., *Circulation*, 90:228–234 (1994) and Takeshita, et al., *J Clin Invest*, 93:662–70 (1994)).

Conversely, there are also.instances, where inhibition of angiogenesis is desirable. For example, many diseases are driven by persistent unregulated angiogenesis. In arthritis, new capillary blood vessels invade the joint and destroy cartilage. In diabetes, new capillaries invade the vitreous, bleed, and cause blindness. Ocular neovascularization is the most common cause of blindness. Tumor growth and metastasis are angiogenesis-dependent. A tumor must continuously stimulate the growth of new capillary blood vessels for the tumor itself to grow.

The current treatment of these diseases is inadequate.

Agents which prevent continued angiogenesis, e.g, drugs (TNP-470), monoclonal antibodies and antisense nucleic acids, are currently being tested. However, new agents that inhibit angiogenesis are need.

Recently, the feasibility of gene therapy for modulating angiogenesis has been demonstrated. For example, promoting angiogenesis in the treatment of ischemia was demonstrated in a rabbit model and in human clinical trials with VEGF using a Hydrogel-coated angioplasty balloon as the gene delivery system. Successful transfer and sustained expression of the VEGF gene in the vessel wall subsequently augmented neovascularization in the ischemic limb (Takeshita, et al., *Laboratory Investigation*, 75:487–502 (1996); Isner, et al., *Lancet*, 348:370 (1996)). In addition, it has been demonstrated that direct intramuscular injection of DNA encoding VEGF into ischemic tissue induces angiogenesis, providing the ischemic tissue with increased blood vessels (U.S. Ser. No. 08/545,998; Tsurumi et al., *Circulation*, In Press).

Alternative methods for regulating angiogenesis are still desirable for a number of reasons. For example, it is believed that native endothelial cell (EC) number and/or viability decreases over time. Thus, in certain patient populations, e.g., the elderly, the resident population of ECs that is competent to respond to administered angiogenic cytokines may be limited.

Moreover, while agents promoting or inhibiting angiogenesis may be useful at one location, they may be undesirable at another location. Thus, means to more precisely regulate angiogenesis at a given location are desirable.

SUMMARY OF THE INVENTION

We have now discovered that by using techniques similar to those employed for HSCs, EC progenitors can be isolated from circulating blood. In vitro, these cells differentiate into ECs. Indeed, one can use a multipotentiate undifferentiated cell as long as it is still capable of becoming an EC, if one adds appropriate agents to result in it differentiating into an EC.

We have also discovered that in vivo, heterologous, homologous, and autologous EC progenitor grafts incorporate into sites of active angiogenesis or blood vessel injury, i.e. they selectively migrate to such locations. This observation was surprising. Accordingly, one can target such sites by the present invention.

The present invention provides a method for regulating angiogenesis in a selected patient in need of a change in the rate of angiogenesis at a selected site. The change in angiogenesis necessary may be reduction or enhancement of angiogenesis. This is determined by the disorder to be treated. In accordance with the method of the present invention, an effective amount of an endothelial progenitor cell or modified version thereof to accomplish the desired result is administered to the patient.

In order to reduce undesired angiogenesis, for example, in the treatment of diseases such as rheumatoid arthritis, psoriasis, ocular neovascularization, diabetic retinopathy, neovascular glaucoma, angiogenesis-dependent tumors and tumor metastasis, a modified endothelial cell, having been modified to contain a compound that inhibits angiogenesis, e.g., a cytotoxic compound or angiogenesis inhibitor, can be administered.

To enhance angiogenesis, for example in the treatment of cerebrovascular ischemia, renal ischemia, pulmonary ischemia, limb ischemia, ischemic cardiomyopathy and myocardial ischemia, endothelial progenitor cells are administered. To further enhance angiogenesis an endothelial progenitor cell modified to express an endothelial cell mitogen may be used. Additionally, an endothelial cell mitogen or a nucleic acid encoding an endothelial cell mitogen can further be administered.

In another embodiment, the present invention provides methods of enhancing angiogenesis or treating an injured blood vessel. In accordance with these methods, endothelial progenitor cells are isolated from the patient, preferably from peripheral blood, and readministering to the patient. The patient may also be treated with endothelial cell mitogens to endothelial cell growth. The vessel injury can be the result of balloon angioplasty, deployment of an endovascular stent or a vascular graft.

The present invention also provides a method of screening for the presence of ischemic tissue or vascular injury in a patient. The method involves contacting the patient with a labelled EC progenitor and detecting the labelled cells at the site of the ischemic tissue or vascular injury.

The present invention also includes pharmaceutical products and kit for all the uses contemplated in the methods described herein.

Other aspects of the invention are disclosed infra.

BRIEF DESCRIPTION OF THE DRAWINGS

FIGS. 1–1G show cell shape and formation.

FIG. 3 shows FACS analysis of freshly isolated $MB^{CD34+}$, $AT^{CD34+}$ after 7 days in culture, and HUVECs. Cells were labeled with FITC using antibodies against CD34, CD31 (Biodesign); Flk-1, Tie-2 (Santa Cruz Biotechnology); and CD45. All results were confirmed by triplicate experiments. Shaded area of each box denotes negative antigen gate, white area denotes positive gate. Numbers indicated for individual gates denote percentage of cells determined by comparison with corresponding negative control labeling.

FIG. 5 is a graph illustrating NO release from $AT^{CD34+}$ was measured with an NO-specific polarographic electrode connected to an NO meter (Iso-NO, World Precision Instruments) (17). Calibration of NO electrode was performed daily before experimental protocol according to the following equation: $2KNO_2+2KI+2H_2SO4 \rightarrow 2NO+I_2+2H_2O+2K_2SO_4$. A standard calibration curve was obtained by adding graded concentrations of $KNO_2$ (0–500 nmol/L) to calibration solution containing KI and $H_2SO4$. Specificity of the electrode to NO was previously documented by measurement of NO from authentic NO gas (18). $AT^{CD34+}$ cultured in 6-well plate were washed and then bathed in 5 ml of filtered Krebs-Henseleit solution. Cell plates were kept on a slide warmer (Lab Line Instruments) to maintain temperature between 35 and 37° C. For NO measurement, sensor probe was inserted vertically into the wells, and the tip of the electrode remained 2 mm under the surface of the solution. Measurement of NO, expressed as pmol/10⁵ cells, was performed in a well with incremental doses of VEGF (1, 10, 100 ng/ml) and Ach (0.1, 1, 10 $\mu$M). HUVECs and bovine aortic ECs were employed as positive controls. For negative control, HCSMCs, NO was not detectable. All values reported represent means of 10 measurements for each group.

FIGS. 6A–6D show co-culture of $MB^{CD34+}$ with HUVECs. Freshly isolated $MB^{CD34+}$ were labeled with Dil dye and plated on a confluent HUVEC monolayer attached to a fibronectin-coated chamber slide at a density of 278 cells/mm² (Nunc). Differentiation of $MB^{CD34+}$ into spindle shaped attaching cells ($AT^{CD34+}$) (red fluorescence) was observed among HUVECs within 12 h (6A). The $AT^{CD34+}$ number increased on monolayer for 3 d (6B), while meshwork structures were observed in some areas (6C). Three days after co-culture, both cells were re-seeded on Matrigel (Becton Dickinson)-coated slides and within 12 h disclosed capillary network formation, consisting of Dil-labeled $AT^{CD34+}$ and HUVECs (6D).

FIGS. 8A–8K show sections retrieved from ischemic hindlimb following in vivo administration of heterologous (FIG. 8A–8H), homologous (8I), and autologous (8J,8K) EC progenitors. (8A,8B) Red fluorescence in small intermuscular artery 6 wks after injection of Dil-labeled $MB^{CD34+}$. Green fluorescence denotes EC-specific lectin UEA-1. (8C). Dil (red) and CD31 (green) in capillaries between muscles, photographed through double filter 4 wks after Dil-labeled $MB^{CD34+}$ injection. (8D) Same capillary structure as in (C), showing CD31 expression by $MB^{CD34+}$ which have been incorporated into host capillary structures expressing CD31. (8E,8F) Immunostaining 2 wks after $MB^{CD34+}$ injection shows capillaries comprised of Dil-labeled $MB^{CD34+}$ derived cells expressing tie-2 receptor (green fluorescence). Most $MB^{CD34+}$ derived cells are tie-2 positive, and are integrated with some tie-2 positive native (host) capillary cells identified by absence of red fluorescence. (8G,8H) Two wks after injection of DiI-labeled $MB_{CD34-}$. Although isolated $MB^{CD34-}$derived cells (red) can be observed between muscles, but these cells do not express CD31.

(8I) Immunohistochemical β-galactosidase staining of muscle harvested from ischemic limb of B6, 129 mice 4 wks following administration of $MB_{Flk-1+}$ isolated from β-galactosidase transgenic mice. Cells overexpressing β-galactosidase (arrows) have been incorporated into capillaries and small arteries; these cells were identified as ECs by anti-CD31 antibody and BS-1 lectin.

(8J,8K) Sections of muscles harvested from rabbit ischemic hindlimb 4 wks after administration of autologous $MB^{CD34+}$. DiI fluorescence (J) indicates localization of $MB^{CD34+}$ derived cells in capillaries seen in phase contrast photomicrograph (8K). Each scale bar indicates 50 μm.

DETAILED DESCRIPTION OF THE INVENTION

We have now discovered a means to regulate angiogenesis, to promote angiogenesis in certain subject populations, and to more precisely target certain tissues. These methods all involve the use of endothelial cell progenitors. One preferred progenitor cell is an angioblast.

Post-natal neovascularization is believed to result exclusively from the proliferation, migration, and remodeling of fully differentiated endothelial cells (ECs) derived from pre-existing native blood vessels (1). This adult paradigm, referred to as angiogenesis, contrasts with vasculogenesis, the term applied to formation of embryonic blood vessels from EC progenitors (2).

In contrast to angiogenesis, vasculogenesis typically begins as a cluster formation, or blood island, comprised of EC progenitors (e.g. angioblasts) at the periphery and hematopoietic stem cells (HSCs) at the center (3). In addition to this intimate and predictable spatial association, such EC progenitors and HSCs share certain common antigenic determinants, including flk-1, tie-2, and CD-34. Consequently, these progenitor cells have been interpreted to derive from a common hypothetical precursor, the hemangioblast (3,4).

The demonstration that transplants of HSCs derived from peripheral blood can provide sustained hematopoietic recovery constitutes inferential evidence for circulating stem cells. (5). This observation is now being exploited clinically as an alternative to bone marrow transplantation.

We have now discovered that by using techniques similar to those employed for HSCs, EC progenitors can be isolated from circulating blood. In vitro, these cells differentiate into ECs. Indeed, one can use a multipotentiate undifferentiated cell as long as it is still capable of becoming an EC, if one adds appropriate agents to result in it differentiating into an EC.

We have also discovered that in vivo, heterologous, homologous, and autologous EC progenitor grafts incorporate into sites of active angiogenesis or blood vessel injury, i.e. they selectively migrate to such locations. This observation was surprising. Accordingly, one can target such sites by the present invention.

In accordance with the present invention, EC progenitors, can be used in a method for regulating angiogenesis, i.e., enhancing or inhibiting blood vessel formation, in a selected patient and in some preferred embodiments for targetting specific locations. For example, the EC progenitors can be used to enhance angiogenesis or to deliver an angiogenesis modulator, e.g. anti- or pro-angiogenic agents, respectively to sites of pathologic or utilitarian angiogenesis. Additionally, in another embodiment, EC progenitors can be used to induce reendothelialization of an injured blood vessel, and thus reduce restenosis by indirectly inhibiting smooth muscle cell proliferation.

In one preferred embodiment the EC cells can be used alone to potentiate a patient for angiogenesis. Some patient population, typically elderly patients, may have either a limited number of ECs or a limited number of functional ECs. Thus, if one desires to promote angiogenesis, for example, to stimulate vascularization by using a potent angiogenesis promotor such as VEGF, such vascularization can be limited by the lack of ECs. However, by administering the EC progenitors one can potentiate the vascularization in those patients.

Accordingly, the present method permits a wide range of strategies designed to modulate angiogenesis such as promoting neovascularization of ischemic tissues (24). EC mitogens such as VEGF and bFGF, for example, have been employed to stimulate native ECs to proliferate, migrate, remodel and thereby form new sprouts from parent vessels (25). A potentially limiting factor in such therapeutic paradigms is the resident population of ECs that is competent to respond to administered angiogenic cytokines. The finding that NO production declines as a function of age (26) may indicate a reduction in EC number and/or viability that could be addressed by autologous EC grafting. The success demonstrated to date with autologous grafts of HSCs derived from peripheral blood (5) supports the clinical feasibility of a "supply side" approach to therapeutic angiogenesis. The in vivo data set forth herein indicate that autologous EC transplants are feasible, and the in vitro experiments indicate that EC progenitors ($MB^{CD34+}$ derived ECs) can be easily manipulated and expanded ex vivo.

Our discovery that these EC progenitors home to foci of angiogenesis makes these cells useful as autologous vectors for gene therapy and diagnosis of ischemia or vacular injury. For example, these cells can be utilized to inhibit as well as augment angiogenesis. For anti-neoplastic therapies, for example, EC progenitors can be transfected with or coupled to cytotoxic agents, cytokines or co-stimulatory molecules to stimulate an immune reaction, other anti-tumor drugs or angiogenesis inhibitors. For treatment of regional ischemia, angiogenesis could be amplified by prior transfection of EC progenitors to achieve constitutive expression of angiogenic cytokines and/or selected matrix proteins (27). In addition, the EC progenitors may be labelled, e.g., radiolabelled, administered to a patient and used in the detection of ischemic tissue or vacular injury.

EC progenitors may be obtained from human mononuclear cells obtained from peripheral blood or bone marrow of the patient before treatment. EC progenitors may also be obtained from heterologous or autologous umbilical cord blood. Peripheral blood is preferred due to convenience. The leukocyte fraction of peripheral blood is most preferred. EC progenitors may be isolated using antibodies that recognize EC progenitor specific antigens on immature human hematopoietic progenitor cells (HSCs). For example, CD34 is commonly shared by EC progenitor and HSCs. CD34 is expressed by all HSCs but is lost by hematopoietic cells as they differentiate (6). It is also expressed by many, including most activated, ECs in the adult (7). Flk-1, a receptor for vascular endothelial growth factor (VEGF) (8), is also expressed by both early HSCs and ECs, but ceases to be expressed in the course of hematopoietic differentiation (9).

To obtain the EC progenitors from peripheral blood about 5 ml to about 500 ml of blood is taken from the patient. Ppreferably, about 50 ml to about 200 ml of blood is taken.

EC progenitors can be expanded in vivo by administration of recruitment growth factors, e.g., GM-CSF and IL-3, to the patient prior to removing the progenitor cells.

Methods for obtaining and using hematopoietic progenitor cells in autologous transplantation are disclosed in U.S. Pat. No. 5,199,942, the disclosure of which is incorporated by reference.

Once the progenitor cells are obtained by a particular separation technique, they may be administered to a selected patient to treat a number of conditions including, for example, unregulated angiogenesis or blood vessel injury. The cells may also be stored in cryogenic conditions. Optionally, the cells may be expanded ex vivo using, for example, the method disclosed by U.S. Pat. No. 5,541,103, the disclosure of which is incorporated by reference.

The progenitor cells are administered to the patient by any suitable means, including, for example, intravenous infusion, bolus injection, and site directed delivery via a catheter. Preferably, the progenitor cells obtained from the patient are readministered. Generally, from about $10^6$ to about $10^{18}$ progenitor cells are administered to the patient for transplantation.

Depending on the use of the progenitor cells, various genetic material may be delivered to the cell. The genetic material that is delivered to the EC progenitors may be genes, for example, those that encode a variety of proteins including anticancer agents. Such genes include those encoding various hormones, growth factors, enzymes, cytokines, receptors, MHC molecules and the like. The term "genes" includes nucleic acid sequences both exogenous and endogenous to cells into which a virus vector, for example, a pox virus such as swine pox containing the human TNF gene may be introduced. Additionally, it is of interest to use genes encoding polypeptides for secretion from the EC progenitors so as to provide for a systemic effect by the protein encoded by the gene. Specific genes of interest include those encoding TNF, TGF-α, TGF-β, hemoglobin, interleukin-1, interleukin-2, interleukin-3, interleukin-4, interleukin-5, interleukin-6, interleukin-7, interleukin-8, interleukin-9, interleukin-10, interleukin-11, interleukin-12 etc., GM-CSF, G-CSF, M-CSF, human growth factor, co-stimulatory factor B7, insulin, factor VIII, factor IX, PDGF, EGF, NGF, IL-ira, EPO, β-globin, EC mitogens and the like, as well as biologically active muteins of these proteins. The gene may further encode a product that regulates expression of another gene product or blocks one or more steps in a biological pathway. In addition, the gene may encode a toxin fused to a polypeptide, e.g., a receptor ligand, or an antibody that directs the toxin to a target, such as a tumor cell. Similarly, the gene may encode a therapeutic protein fused to a targeting polypeptide, to deliver a therapeutic effect to a diseased tissue or organ.

The cells can also be used to deliver genes to enhance the ability of the immune system to fight a particular disease or tumor. For example, the cells can be used to deliver one or more cytokines (e.g., IL-2) to boost the immune system and/or one or more antigens.

These cells may also be used to selectively administer drugs, such as an antiangiogenesis compound such as O-chloroacetyl carbamoyl fumagillol (TNP-470). Preferably the drug would be incorporated into the cell in a vehicle such as a liposome, a timed released capsule, etc. The EC progenitor would then selectively hone in on a site of active angiogenesis such as a rapidly growing tumor where the compound would be released. By this method, one can reduce undesired side effects at other locations.

In one embodiment, the present invention may be used to enhance blood vessel formation in ischemic tissue, i.e., a tissue having a deficiency in blood as the result of an ischemic disease. Such tissues can include, for example, muscle, brain, kidney and lung. Ischemic diseases include, for example, cerebrovascular ischemia, renal ischemia, pulmonary ischemia, limb ischemia, ischemic cardiomyopathy and myocardial ischemia.

If it is desirable to further enhance angiogenesis, endothelial cell mitogens may also be administered to the patient in conjunction with, or subsequent to, the administration of the EC progenitor cells. Endothelial cell mitogens can be administered directly, e.g., intra-arterially, intramuscularly, or intravenously, or nucleic acid encoding the mitogen may be used. See, Baffour, et al., supra (bFGF); Pu, et al, *Circulation*, 88:208–215 (1993) (aFGF); Yanagisawa-Miwa, et al., supra (bFGF); Ferrara, et al., *Biochem. Biophys. Res. Commun.*, 161:851–855 (1989) (VEGF); (Takeshita, et al., *Circulation*, 90:228–234 (1994)).

The nucleic acid encoding the EC mitogen can be administered to a blood vessel perfusing the ischemic tissue or to a site of vascular injury via a catheter, for example, a hydrogel catheter, as described by U.S. Ser. No. 08/675,523, the disclosure of which is herein incorporated by reference. The nucleic acid also can be delivered by injection directly into the ischemic tissue using the method described in U.S. Ser. No. 08/545,998.

As used herein the term "endothelial cell mitogen" means any protein, polypeptide, mutein or portion that is capable of, directly or indirectly, inducing endothelial cell growth. Such proteins include, for example, acidic and basic fibroblast growth factors (aFGF and bFGF), vascular endothelial growth factor (VEGF), epidermal growth factor (EGF), transforming growth factor α and β (TGF-α and TFG-β), platelet-derived endothelial growth factor (PD-ECGF), platelet-derived growth factor (PDGF), tumor necrosis factor α (TNF-α), hepatocyte growth factor (HGF), insulin like growth factor (IGF), erythropoietin, colony stimulating factor (CSF), macrophage-CSF (M-CSF), granulocyte/macrophage CSF (GM-CSF) and nitric oxidesynthase (NOS). See, Klagsbrun, et al., *Annu. Rev. Physiol.*, 53:217–239 (1991); Folkman, et al., *J. Biol. Chem.*, 267:10931–10934 (1992) and Symes, et al., *Current Opinion in Lipidology*, 5:305–312 (1994). Muteins or fragments of a mitogen may be used as long as they induce or promote EC cell growth.

Preferably, the endothelial cell mitogen contains a secretory signal sequence that facilitates secretion of the protein. Proteins having native signal sequences, e.g., VEGF, are preferred. Proteins that do not have native signal sequences, e.g., bFGF, can be modified to contain such sequences using routine genetic manipulation techniques. See, Nabel et al., *Nature*, 362:844 (1993).

The nucleotide sequence of numerous endothelial cell mitogens, are readily available through a number of computer data bases, for example, GenBank, EMBL and Swiss-Prot. Using this information, a DNA segment encoding the desired may be chemically synthesized or, alternatively, such a DNA segment may be obtained using routine procedures in the art, e.g, PCR amplification. A DNA encoding VEGF is disclosed in U.S. Pat. No. 5,332,671, the disclosure of which is herein incorporated by reference.

In certain situations, it may be desirable to use nucleic acids encoding two or more different proteins in order optimize the therapeutic outcome. For example, DNA encoding two proteins, e.g., VEGF and bFGF, can be used, and provides an improvement over the use of bFGF alone. Or an angiogenic factor can be combined with other genes or their encoded gene products to enhance the activity of targeted cells, while simultaneously inducing angiogenesis, including, for example, nitric oxide synthase, L-arginine, fibronectin, urokinase, plasminogen activator and heparin.

The term "effective amount" means a sufficient amount of compound, e.g. nucleic acid delivered to produce an adequate level of the endothelial cell mitogen, i.e., levels capable of inducing endothelial cell growth and/or inducing angiogenesis. Thus, the important aspect is the level of mitogen expressed. Accordingly, one can use multiple transcripts or one can have the gene under the control of a promoter that will result in high levels of expression. In an alternative embodiment, the gene would be under the control of a factor that results in extremely high levels of expression, e.g., tat and the corresponding tar element.

The EC progenitors may also be modified ex vivo such that the cells inhibit angiogenesis. This can be accomplished, for example, by introducing DNA encoding angiogenesis inhibiting agents to the cells, using for example the gene transfer techniques mentioned herein. Angiogenesis inhibiting agents include, for example, proteins such as thrombospondin (Dameron et al., *Science* 265:1582–1584 (1994)), angiostatin (O'Reilly et al., *Cell* 79:315–328 (1994), IFN-alpha (Folkman, J. *Nature Med.* 1:27–31 (1995)), transforming growth factor beta, tumor necrosis factor alpha, human platelet factor 4 (PF4); substances which suppress cell migration, such as proteinase inhibitors which inhibit proteases which may be necessary for penetration of the basement membrane, in particular, tissue inhibitors of metalloproteinase TIMP-1 and TIMP-2; and other proteins such as protamine which has demonstrated angiostatic properties, decoy receptors, drugs such as analogues of the angioinhibin fumagillin, e.g., TNP-470 (Ingber et al., Nature 348:555–557 (1990), antibodies or antisense nucleic acid against angiogenic cytokines such as VEGF. Alternatively, the cells may be coupled to such angiogenesis inhibiting agent.

If the angiogenesis is associated with neoplastic growth the EC progenitor cell may also be transfected with nucleic acid encoding, or coupled to, anti-tumor agents or agents that enhance the immune system. Such agents include, for example, TNF, cytokines such as interleukin (IL) (e.g., IL-2, IL-4, IL-10, IL-12), interferons (IFN) (e.g., IFN-γ) and co-stimulatory factor (e.g., B7). Preferably, one would use a multivalent vector to deliver, for example, both TNF and IL-2 simultaneously.

The nucleic acids are introduced into the EC progenitor by any method which will result in the uptake and expression of the nucleic acid by the cells. These can include vectors, liposomes, naked DNA, adjuvant-assisted DNA, catheters, gene gun, etc. Vectors include chemical conjugates such as described in WO 93/04701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector [Geller, A. I. et al., *J. Neurochem*, 64:487 (1995); Lim, F., et al., in DNA Cloning: *Mammalian Systems*, D. Glover, Ed. (Oxford Univ. Press, Oxford England) (1995); Geller, A. I. et al., *Proc Natl. Acad. Sci.*: U.S.A.:90 7603 (1993); Geller, A. I., et al., *Proc Natl. Acad. Sci USA*: 87:1149 (1990)], Adenovirus Vectors [LeGal LaSalle et al., *Science*, 259:988 (1993); Davidson, et al., *Nat. Genet*3: 219 (1993); Yang, et al., *J. Virol.* 69: 2004 (1995)] and Adeno-associated Virus Vectors [Kaplitt, M. G., et al., *Nat. Genet.* 8:148 (1994)].

Pox viral vectors introduce the gene into the cells cytoplasm. Avipox virus vectors result in only a short term expression of the nucleic acid. Adehovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofecton, cell microinjection, viral vectors and use of the "gene gun".

To simplify the manipulation and handling of the nucleic acid encoding the protein, the nucleic acid is preferably inserted into a cassette where it is operably linked to a promoter. The promoter must be capable of driving expression of the protein in cells of the desired target tissue. The selection of appropriate promoters can readily be accomplished. Preferably, one would use a high expression promoter. An example of a suitable promoter is the 763-base-pair cytomegalovirus (CMV) promoter. The Rous sarcoma virus (RSV) (Davis, et al., *Hum Gene Ther* 4:151 (1993)) and MMT promoters may also be used. Certain proteins can expressed using their native promoter. Other elements that can enhance expression can also be included such as an enhancer or a system that results in high levels of expression such as a tat gene and tar element. This cassette can then be inserted into a vector, e.g., a plasmid vector such as pUC118, pBR322, or other known plasmid vectors, that includes, for example, an *E. coli* origin of replication. See, Sambrook, et al., *Molecular Cloning: A Laboratory Manual*, Cold Spring Harbor Laboratory press, (1989). The plasmid vector may also include a selectable marker such as the, β-lactamase gene for ampicillin resistance, provided that the marker polypeptide does not adversely effect the metabolism of the organism being treated. The cassette can also be bound to a nucleic acid binding moiety in a synthetic delivery system, such as the system disclosed in WO 95/22618.

If desired, the preselected compound, e.g. a nucleic acid such as DNA may also be used with a microdelivery vehicle such as cationic liposomes and adenoviral vectors. For a review of the procedures for liposome preparation, targeting and delivery of contents, see Mannino and Gould-Fogerite,

*BioTechniques*, 6:682 (1988). See also, Felgner and Holm, *Bethesda Res. Lab. Focus*, 11(2):21 (1989) and Maurer, R. A., *Bethesda Res. Lab. Focus*, 11(2):25 (1989).

Replication-defective recombinant adenoviral vectors, can be produced in accordance with known techniques. See, Quantin, et al., *Proc. Natl. Acad. Sci. USA*, 89:2581–2584 (1992); Stratford-Perricadet, et al., *J. Clin. Invest.*, 90:626–630 (1992); and Rosenfeld, et al., *Cell*, 68:143–155 (1992).

The effective dose of the nucleic acid will be a function of the particular expressed protein, the target tissue, the patient and his or her clinical condition. Effective amount of DNA are between about 1 and 4000 μg, more preferably about 1000 and 2000, most preferably between about 2000 and 4000.

Alternatively, the EC progenitors may be used to inhibit angiogenesis and/or neoplastic growth by delivering to the site of angiogenesis a cytotoxic moiety coupled to the cell. The cytotoxic moiety may be a cytotoxic drug or an enzymatically active toxin of bacterial, fungal or plant origin, or an enzymatically active polypeptide chain or fragment ("A chain") of such a toxin. Enzymatically active toxins and fragments thereof are preferred and are exemplified by diphtheria toxin A fragment, non-binding active fragments of diphtheria toxin, exotoxin A (from *Pseudomonas aeruginosa*), ricin A chain, abrin A chain, modeccin A chain, alphasarcin, certain *Aleurites fordii* proteins, certain Dianthin proteins, *Phytolacca americana* proteins (PAP, PAPII and PAP-S), *Momordica charantia* inhibitor, curcin, crotin, *Saponaria officinalis* inhibitor, gelonin, mitogellin, restrictocin, phenomycin, and enomycin, Ricin A chain, *Pseudomonas aeruginosa* exotoxin A and PAP are preferred.

Conjugates of the EC progenitors and such cytotoxic moieties may be made using a variety of coupling agents. Examples of such reagents are N-succinimidyl-3-(2-pyridyldithio)propionate (SPDP), iminothiolane (IT), bifunctional derivatives of imidoesters such as dimethyl adeipimidate HCl, active esters such as disuccinimidyl suberate, aldehydes such as glutaradehyde, bis-azido compounds such as bis(p-diazoniumbenzoyl)-ethylenediamine, diisocyanates such as tolylene 2,6-diisocyante, and bis-active fluorine compounds such as 1,5-difluoro-2,4-dinitrobenzene.

The enzymatically active polypeptide of the toxins may be recombinantly produced. Recombinantly produced ricin toxin A chain (rRTA) may be produced in accordance with the methods disclosed in PCT W085/03508 published Aug. 15, 1985. Recombinantly produced diphtheria toxin A chain and non-binding active fragments thereof are also described in PCT WO85/03508 published Aug. 15, 1985.

The methods of the present invention may be used to treat blood vessel injuries that result in denuding of the endothelial lining of the vessel wall. For example, primary angioplasty is becoming widely used for the treatment of acute myocardial infarction. In addition, endovascular stents are becoming widely used as an adjunct to balloon angioplasty. Stents are useful for rescuing a sub-optimal primary result as well as for diminishing restenosis. To date, however, the liability of the endovascular prosthesis has been its susceptibility to thrombotic occlusion in approximately 3% of patients with arteries 3.3 mm or larger. If patients undergo stent deployment in arteries smaller than this the incidence of sub-acute thrombosis is even higher. Sub-acute thrombosis is currently prevented only by the aggressive use of anticoagulation. The combination of vascular intervention and intense anticoagulation creates significant risks with regard to peripheral vascular trauma at the time of the stent/angioplasty procedure. Acceleration of reendothelialization by adminstration of EC progenitors to a patient undergoing, or subsequent to, angioplasty and/or stent deployment can stabilize an unstable plaque and prevent re-occlusion.

The method of the present invention may be used in conjunction with the method for the treatment of vascular injury diclosed in PCT/US96/15813.

In addition, the methods of the present invention may be used to accelerate the healing of graft tissue, e.g., vascular grafts.

The present invention also includes pharmaceutical products for all the uses contemplated in the methods described herein. For example, there is a pharmaceutical product, comprising nucleic acid encoding an endothelial cell mitogen and EC progenitors, in a physiologically acceptable administrable form.

The present invention further includes a kit for the in vivo systemic introduction of an EC progenitor and an endothelial cell mitogen or nucleic acid encoding the same into a patient. Such a kit includes a carrier solution, nucleic acid or mitogen, and a means of delivery, e.g., a catheter or syringe. The kit may also include instructions for the administration of the preparation.

All documents mentioned herein are incorporated by reference herein in their entirety.

The present invention is further illustrated by the following examples. These examples are provided to aid in the understanding of the invention and are not construed as a limitation thereof.

EXAMPLES

Method and Materials

Human peripheral blood was obtained using a 20 gauge intravenous catheter, discarding the first 3 ml. Leukocyte fraction of blood was obtained by Ficoll density gradient centrifugation and plated on plastic tissue culture for 1 hr to avoid contamination by differentiated adhesive cells.

Fluorescent activated cell sorting (FACS) was carried out with $>1\times10^6$ CD34 positive and negative mononuclear blood cells ($MB^{CD34+}$, $MB^{CD34-}$). Cells were analyzed with Becton-Dickinson FACS sorter and the lysis II analysis program using antibodies to CD34 (Biodesign).

M-199 medium with 20% FBS and bovine brain extract (Clonetics) was used as standard medium for all cell culture experiments.

C57BL/6J×129/SV background male mice (Hirlan), 3 mo old and 20–30 g, were used in these experiments (n=24). Animals were anesthetized with 160 mg/kg intraperitoneally of pentobarbital. The proximal end of one femoral artery and distal portion of the corresponding saphenous artery were ligated, following which the artery, as well as all side-branches, were dissected free and excised. (All protocols were approved by St. Elizabeth's Institutional Animal Care and Use Committee.)

New Zealand White rabbits (3.8–4.2 kg, n=4, Pine Acre Rabbitry) were anesthetized with a mixture of ketainine (50 mg/kg) and acepromazine (0.8 mg/kg) following premedication with xylazine (2 mg/kg). After a longitudinal incision, the femoral artery was dissected free along its entire length; all branches of the femoral artery were also dissected free. After ligating the popliteal and saphenous arteries distally, the external iliac artery proximally and all femoral arterial branches, the femoral artery was completely excised (23).

Isolation and Analysis

CD34 positive mononuclear blood cells ($MB^{CD34+}$) were isolated from peripheral blood by CD34 antibody-coated magnetic beads (Dynal) as described above.

FACS analysis indicated that 15.9±3.3% of selected cells versus <0.1% of the remaining cells expressed CD34. Depleted ($MB^{CD34-}$) cells were used as controls. Flk-1 antibody was used for magnetic bead selection of Flk-1 positive mononuclear blood cells ($MB^{Flk1+}$).

Figure 1A:
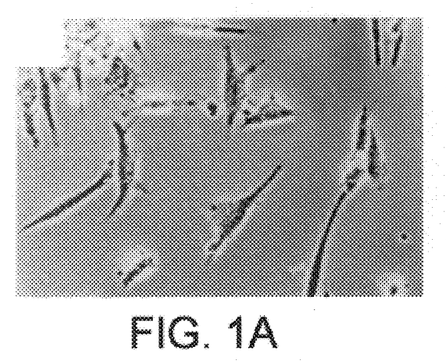
FIG. 1A shows spindle shaped attaching cells ($AT^{CD34+}$) 7 days after plating $MB^{CD34+}$ on fibronectin with standard medium (10). Network formation (1B) and cord-like structures (1C) were observed 48 h after plating co-culture of $MB^{CD34+}$, labeled with Dil dye (Molecular Probe), and unlabeled $MB^{CD34-}$ (ratio of 1:100) on fibronectin-coated dish. These cords consisted principally of Dil-labeled $MB^{CD34+}$ derived cells ($AT^{CD34+}$). Beginning 12 h after co-culture, $MB^{CD34+}$ derived cells demonstrated multiple foci of cluster formation (1D, 1E,). $AT^{CD34+}$ sprout from the periphery, while round cells remain in the center and detach from the cluster several days later. After 5 d, uptake of acLDL-Dil (Molecular Probe) was seen in $AT^{CD34+}$ at the periphery but not the center of the cluster (1F, 1G).
Figure 2:
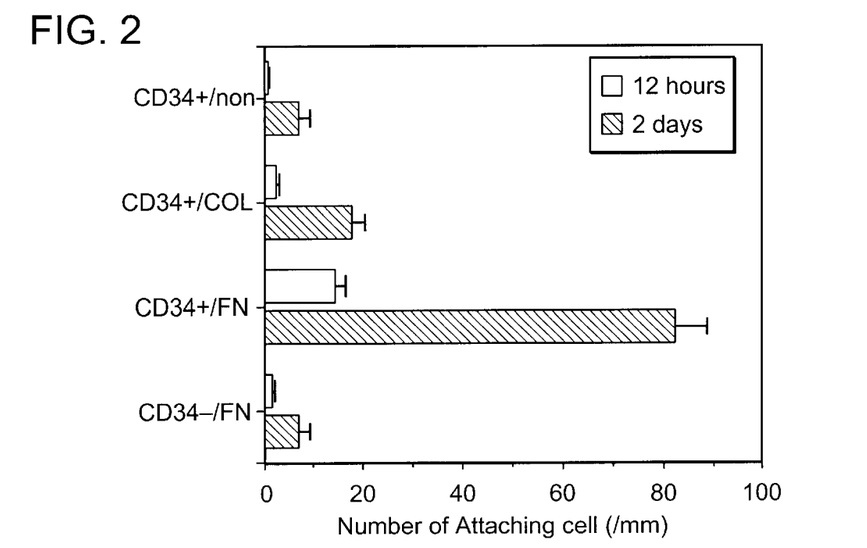
FIG. 2 shows the number of $AT^{CD34+}$ 12 h and 3 d after single culture of $MB^{CD34+}$ on plastic alone (CD34+/non), collagen coating (CD34+/COL), or fibronectin. (CD34+/FN), and $MB^{CD34-}$ on fibronectin (CD34−/FN). $AT^{CD34+}$ yielded significantly higher number of cells at 12 h and 3 d when plated on fibronectin (p<0.05, by ANOVA).

$MB^{CD34+}$ and $MB^{CD34-}$ were plated separately in standard medium on tissue culture plastic, collagen type I, or fibronectin. When plated on tissue culture plastic or collagen at a density of $1\times10^3/mm^2$, a limited number of $MB^{CD34+}$ attached, and became spindle shaped and proliferated for 4 wks. A subset of $MB^{CD34+}$ plated on fibronectin promptly attached and became spindle shaped within 3 days (FIG. 1A); the number of attaching cells ($AT^{CD34+}$) in culture increased with time (FIG. 2). Attached cells were observed only sporadically among cultures of $MB^{CD34-}$, including cells followed for up to 4 wks on fibronectin-coated plates.

Figure 1B:
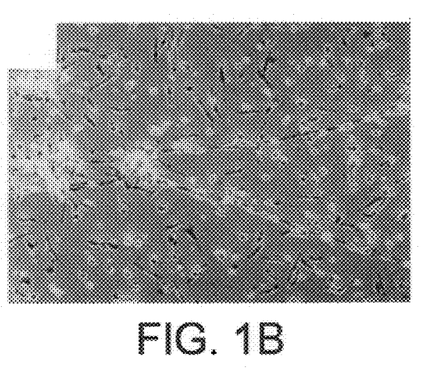
Figure 1C:
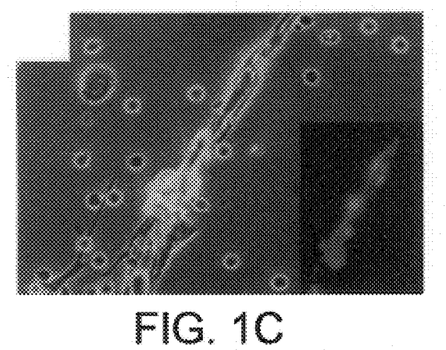
Figure 1D:
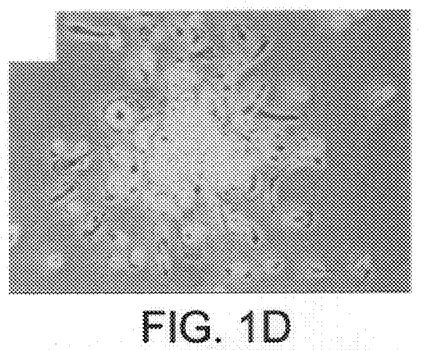
Figure 1E:
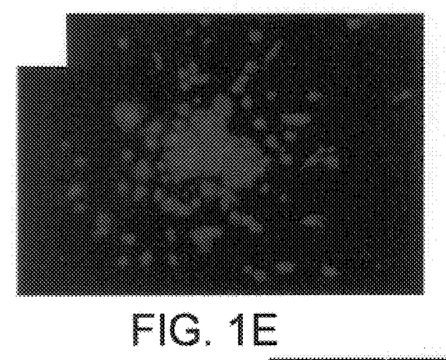
Figure 1F:
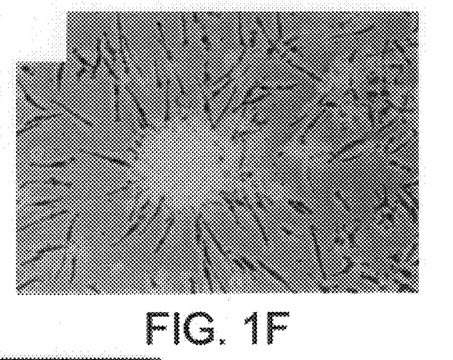
Figure 1G:
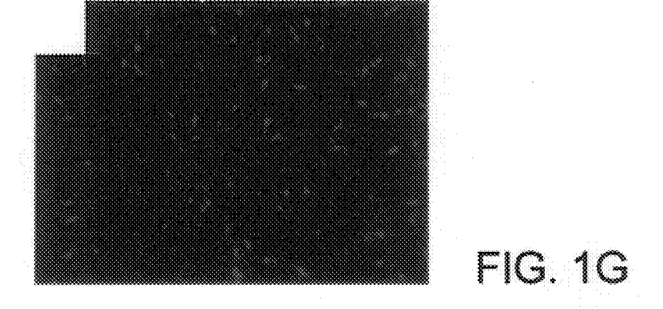

To confirm that spindle-shaped cells were derived from CD34 positive-cells, $MB^{CD34+}$ were labeled with the fluorescent dye, DiI, and co-plated with unlabeled $MB^{CD34-}$ on fibronectin at an overall density of $5\times10^3/mm^2$; ratio of the two cell types was identical to that of the original mononuclear cell population (1% $MB^{CD34+}$, 99% $MB^{CD34-}$). Seven days later, DiI-labeled cells derived from $MB^{CD34+}$, initially accounting for only 1% of blood cells, accounted for 60.3±4.7% of total attaching cells analyzed by FACS. Co-incubation with $MB^{CD34+}$ increased proliferation to >10×$MB^{CD34+}$ plated alone at a cell density of $5\times10/mm^2$ cell (d 3=131.3±26.8 vs 9.7±3.5/$mm^2$). $MB^{CD34+}/MB^{CD34-}$ co-cultures also enhanced $MB^{CD34+}$ differentiation, including formation of cellular networks and tube-like structures on fibronectin-coated plates (FIGS. 1B,C). These structures consisted principally of DiI-labeled $MB^{CD34+}$ derived cells (FIG. 1C). Moreover, within 12 h of co-culture, multiple cluster formations were observed (FIG. 1D), consisting principally of DiI-labeled $MB^{CD34+}$ derived cells (FIG. 1E). These clusters were comprised of round cells centrally, and sprouts of spindle-shaped cells at the periphery. The appearance and organization of these clusters resembled that of blood island-like cell clusters observed in dissociated quail epiblast culture, which induced ECs and gave rise to vascular structures in vitro (3). $AT^{CD34+}$ at the cluster periphery were shown to take up DiI-labeled acetylated LDL, characteristic of EC lineage (13), whereas the round cells comprising the center of cluster did not (FIGS. 1F,G); the latter detached from the cluster several days later. Similar findings were observed in the experiments using $MB^{Flk1+}$.

Expression of Leukocyte and EC Markers

Figure 3:
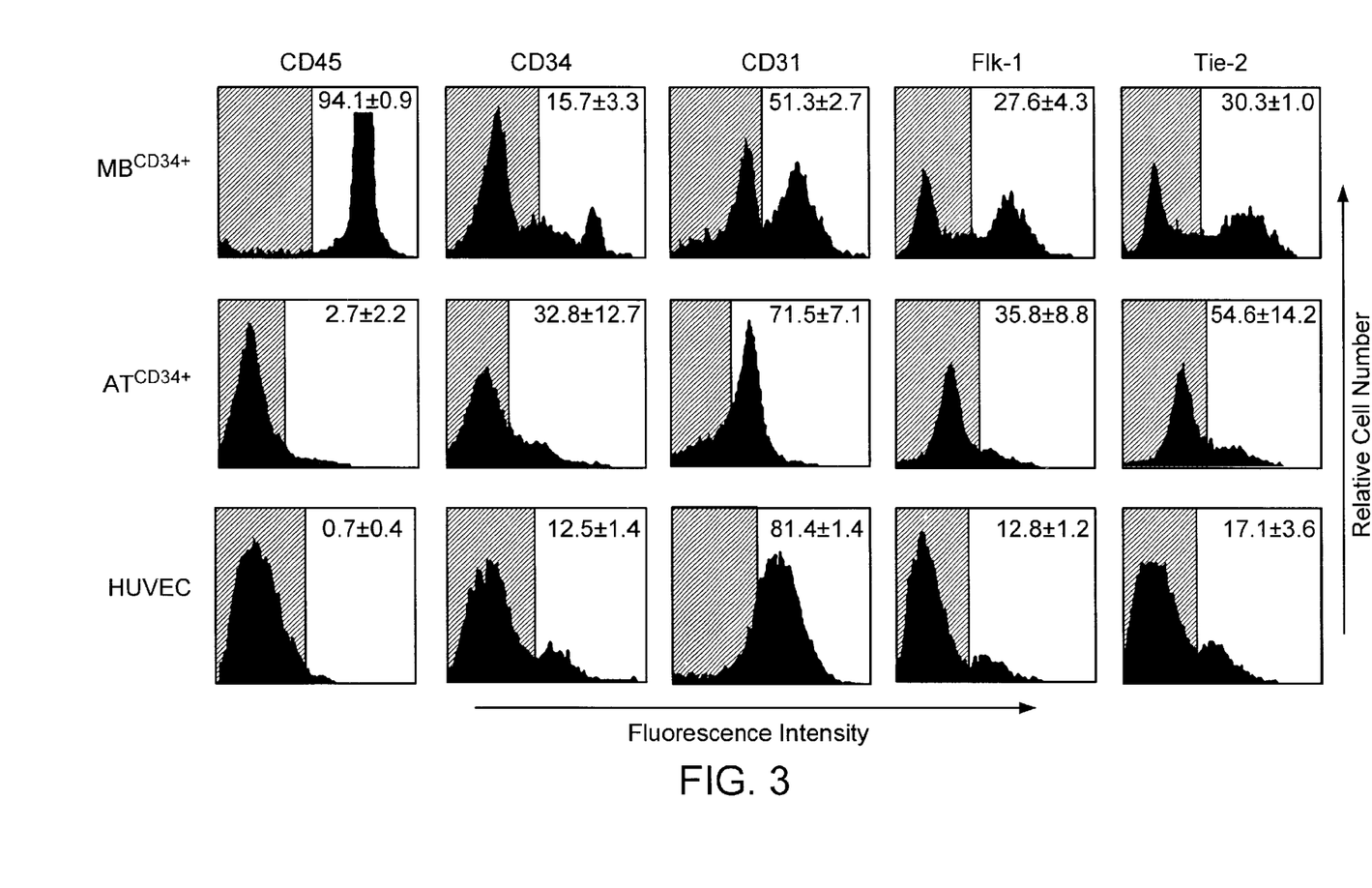

To further evaluate progression of $MB^{CD34+}$ to an EC-like phenotype, cells were assayed for expression of leukocyte and EC markers. Freshly isolated $MB^{CD34+}$ versus $AT^{CD34+}$ cultured at densities of $1\times10^3$ cell/$mm^2$ for 7 days were incubated with fluorescent-labeled antibodies and analyzed by FACS (FIG. 3). Leukocyte common antigen, CD45, was identified on 94.1% of freshly isolated cells, but was essentially lost by 7 d in culture (FIG. 3). Augmented expression of UEA-1, CD34, CD31, Flk-1, Tie-2 and E-selectin—all denoting EC lineage (14)—was detected among $AT^{CD34+}$ after 7 days in culture, compared to freshly isolated $MB^{CD34+}$. CD68 expression, suggesting monocyte/macrophage lineage, was limited to 6.0±2.4% cells.

Expression of Factor VIII, UEA-1, CD31, ecNOS, and E-selectin was also documented by immunohistochemistry for $AT^{CD34+}$ after 7 days culture (data not shown). After 3, 7, and 14 days in culture, more than 80% $AT^{CD34+}$ took up DiI-labeled acLDL (13).

Figure 4:
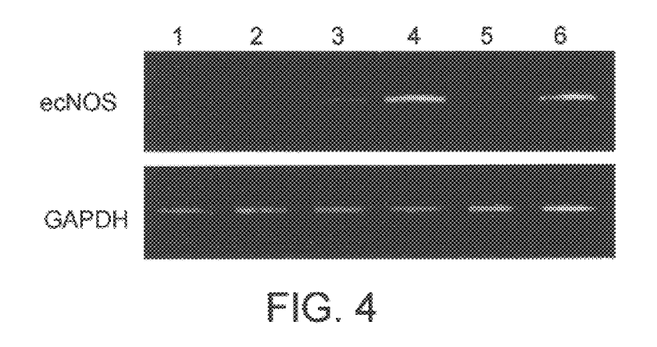
FIG. 4 shows expression of ecNOS mRNA in $MB^{CD34-}$, $MB^{CD34+}$, $AT^{CD34+}$, human coronary smooth muscle cells (HCSMCs) and HUVECs. DNA was reverse transcribed from ≈1×10⁶ cells each. Equal aliquots of the resulting DNA were amplified by PCR (40 cycles) with paired primers (sense/antisense: AAG ACA TTT TCG GGC TCA CGC TGC GCA CCC/TGG GGT AGG CAC TTT AGT AGT TCT CCT AAC, SEQ ID NO:1) to detect ecNOS mRNA. Equal aliquots of the amplified product were analyzed on a 1% agarose gel. Only a single band was observed, corresponding to the expected size (548 bp) for ecNOS. Lane 1=$MB_{CD34-}$, Lane 2=$MB^{CD34+}$, Lane 3=$AT_{CD34+}$ after 3d, Lane 4=$AT^{CD34+}$ after 7d, Lane 5=HCSMCs, Lane 6=HUVECs.
Figure 5:
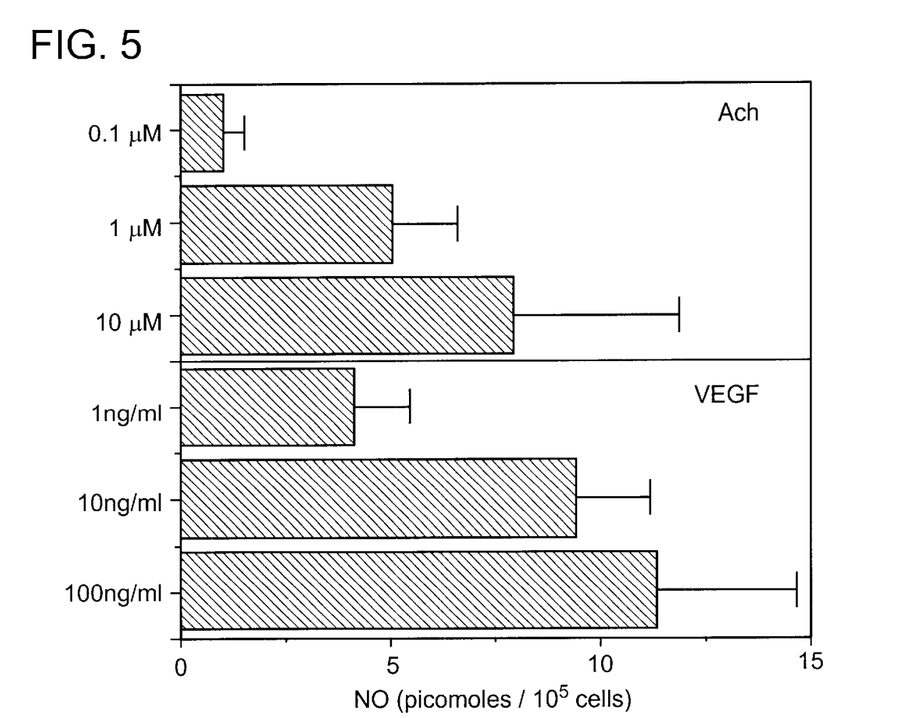

ECs uniquely express endothelial constitutive nitric oxide synthase (ecNOS). Accordingly, $MB^{CD34+}$, $MB^{CD34-}$ and $AT^{CD34+}$ were investigated for expression of ecNOS by RT-PCR (15). ecNOS mRNA was not detectable among $MB^{CD34-}$ and was present at very low levels in freshly isolated $MB^{CD34+}$ (FIG. 4). In $AT^{CD34+}$ cultured for 7 d, however, ecNOS mRNA was markedly increased (FIG. 5). Functional evidence of ecNOS protein in $AT^{CD34+}$ was documented by measurement of nitric oxide in response to the EC-dependent agonist, acetylcholine (Ach), and the EC-specific mitogen, vascular endothelial growth factor (VEGF) (16) (FIG. 5); the latter parenthetically constitutes evidence for a functional Flk-1 receptor as well among $AT^{CD34+}$.

Cell-Cell Interaction

Figures 6A, 6B, 6D:
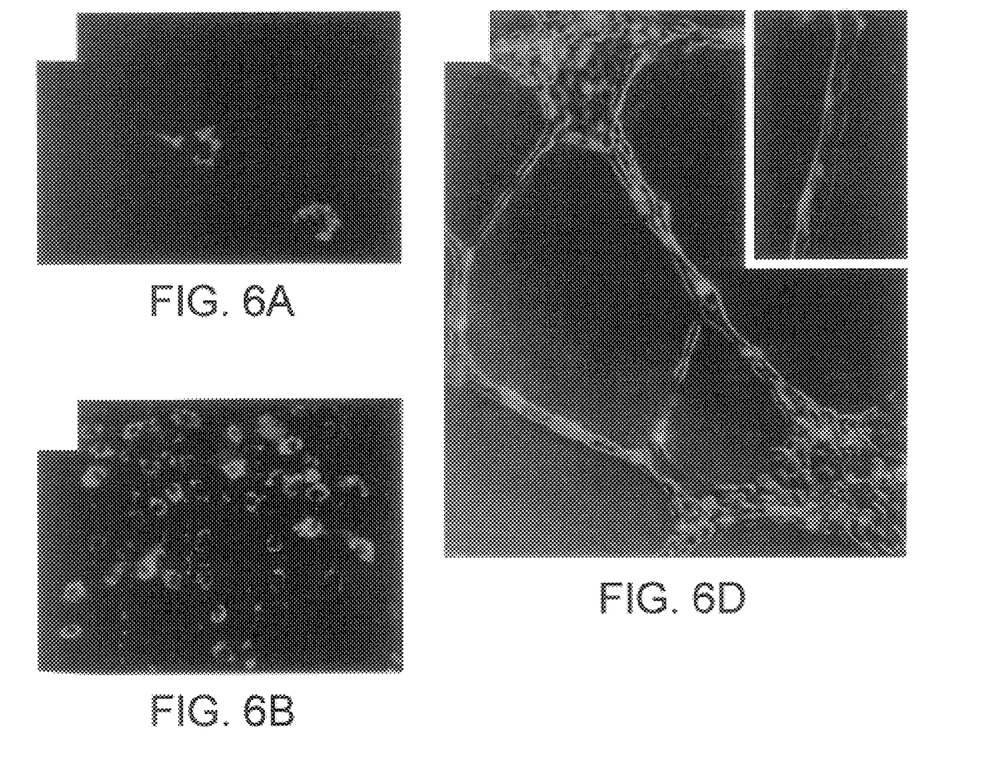
Figure 6C:
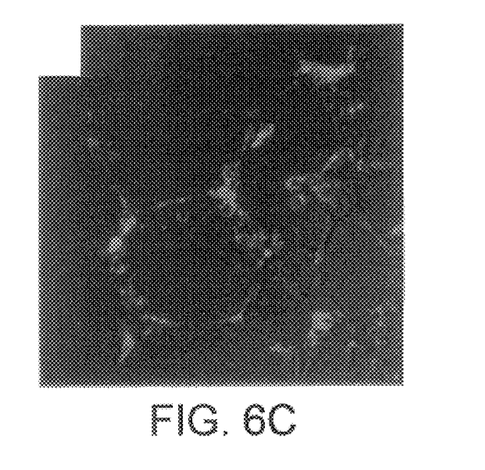
Figure 7:
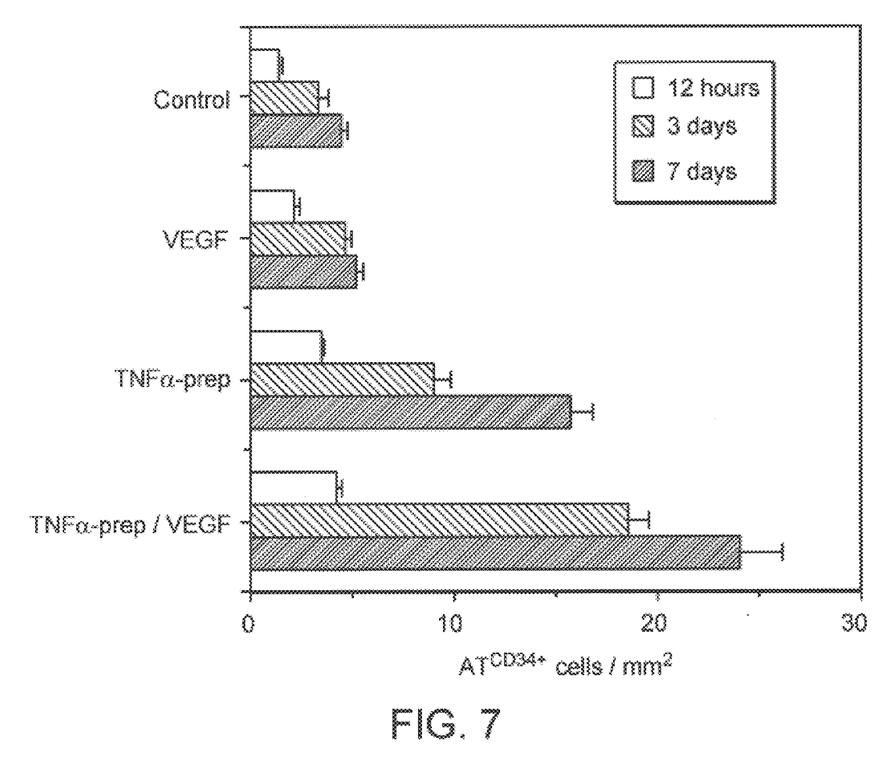
FIG. 7 shows the effect of activated ECs and VEGF on $MB^{CD34+}$ differentiation was investigated by pretreatment of HUVEC with TNF-α (20 ng/ml) for 12 h, and/or incubation of $AT^{CD34+}$/HUVEC co-culture with VEGF (50 ng/ml).

Cell-cell interaction is considered to play a decisive role in cell signaling, differentiation, and proliferation during hematopoiesis (19) and angiogenesis (20). To study the impact of $MB^{CD34+}$ interaction with mature ECs on the differentiation of $MB^{CD34+}$ into an EC-like phenotype, DiI-labeled $MB^{CD34+}$ were plated on a confluent HUVEC monolayer. Adherent, labeled cells were found throughout the culture within 12 h (FIG. 6A), and increased in number for up to 3 d (FIG. 6B). When incubated with 50 ng/ml VEGF and 10 ng/ml bFGF, a meshwork of cord-like structures comprised of both DiI-labeled and unlabeled cells could be seen within 3 d after co-culture (FIG. 6C). Both cell types were then re-seeded on Matrigel (Becton Dickinson) coated slides and within 12 h demonstrated formation of capillary networks comprised of DiI-labeled $MB^{CD34+}$ derived cells and HUVECs (FIG. 6D). To facilitate cell-cell interaction, HUVECs were pre-treated with TNF-$\alpha_{13}$ (21), resulting in increased numbers of $AT^{CD34+}$ (FIG. 6E); synergistic augmentation was observed upon co-incubation with VEGF. Identically treated co-cultures of HUVECs and DiI-labeled $MB^{CD34-}$ yielded desquamated labeled cells and/or no cords. Similar findings were observed when EC precursors were isolated using $MB^{Flk1+}$.

In Vivo Angiogenesis

Figure 8A:
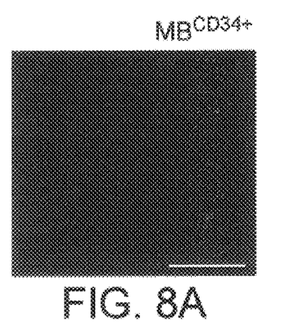

Previous studies have established that ECs constitute the principal cell responsible for in, vivo angiogenesis (1). To determine if $MB^{CD34+}$ can contribute to angiogenesis in vivo, we employed two previously characterized animal models of hindlimb ischemia. For administration of human $MB^{CD34+}$, C57BL/6J×129/SV background athymic nude mice were employed to avoid potential graft-versus host complications. Two days later, when the limb was severely ischemic, mice were injected with $5\times10^5$ DiI-labeled human $MB^{CD34+}$ or $MB^{CD34-}$ via the tail vein. Histologic sections of limbs examined 1, 2, 4, and 6 wks later for the presence of DiI labeled cells revealed numerous DiI-labeled cells in the neo-vascularized ischemic hindlimb. Labeled cells were more numerous in $MB^{CD34+}$ versus $MB^{CD34-}$ injected mice, and almost all labeled cells appeared to be integrated into capillary vessel walls (FIGS. 8A,C,E,G).

Figure 8B:
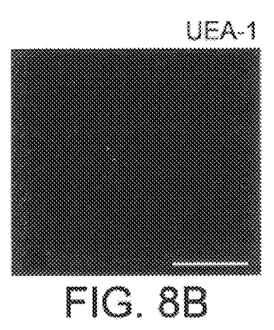
Figure 8C:
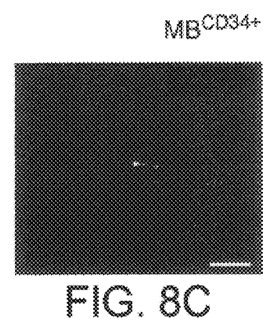
Figure 8D:
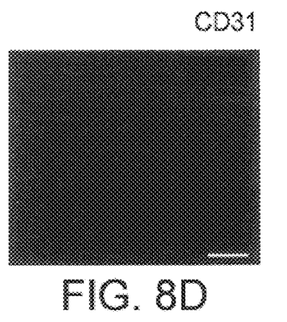
Figure 8E:
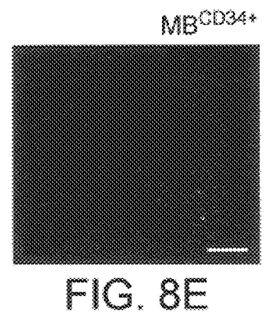
Figure 8F:
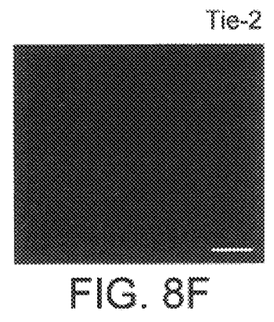
Figure 8G:
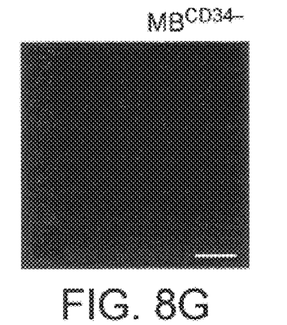
Figure 8H:
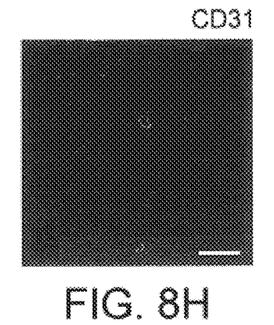

No labeled cells were observed in the uninjured limbs of either $MB^{CD34+}$ or $MB^{CD34-}$ injected mice. DiI labeled cells were also consistently co-labeled with immunostains for UEA-1 lectin (FIG. 8B), CD31 (FIG. 85D), and Tie-2 (FIG. 8F). In contrast, in hindlimb sections from mice injected with $MB^{CD34-}$, labeled cells were typically found in stroma near capillaries, but did not form part of the vessel wall, and did not label with UEA-1 or anti-CD31 antibodies (FIGS. 8G,H).

Figure 8I:
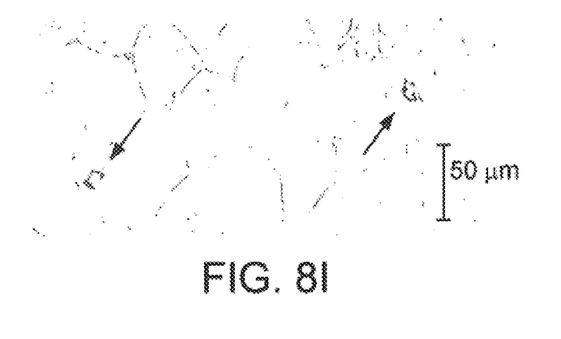

A transgenic mouse overexpressing β-galactosidase was then used to test the hypothesis that homologous grafts of EC progenitors could contribute to neovascularization in vivo. Flk-1 cell isolation was used for selection of EC progenitors due to lack of a suitable anti-mouse CD34 antibody. Approximately $1 \times 10^4$ $MB^{Flk+}$ were isolated from whole blood of 10 βgalactosidase transgenic mice with B6, 129 genetic background. $MB^{Flk1+}$ or the same number of $MB^{Flk1-}$ were injected into B6, 129 mice with hindlimb ischemia of 2 days duration. Immunostaining of ischemic tissue for, β-galactosidase, harvested 4 wks after injection, demonstrated incorporation of cells expressing β-galactosidase in capillaries and small arteries (FIG. 8I); these cells were identified as ECs by staining with anti-CD31 antibody and BS-1 lectin.

Figure 8J:
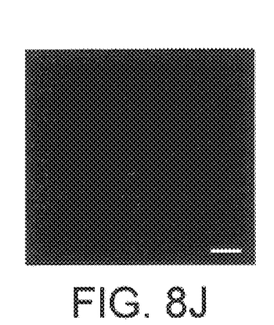
Figure 8K:
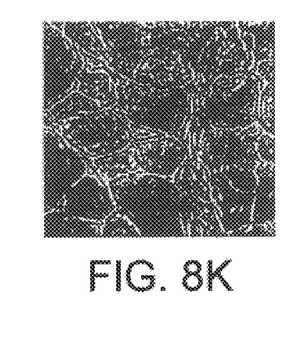

Finally, in vivo incorporation of autologous $MB^{CD34+}$ into foci of neovascularization was tested in a rabbit model of unilateral hindlimb ischemia. $MB^{CD34+}$ were isolated from 20 ml of blood obtained by direct venipuncture of normal New Zealand white rabbits immediately prior to surgical induction of unilateral hindlimb ischemia. Immediately following completion of the operative procedure, freshly isolated autologous DiI-labeled $MB^{CD34+}$ were re-injected into the ear vein of the same rabbit from which the blood had been initially obtained. Four wks after ischemia, histologic sections of the ischemic limbs were examined. DiI-labeled cells were localized exclusively to neovascular zones of the ischemic limb, incorporated into capillaries and consistently expressing CD31 and UEA-1 (FIGS. 8J,K).

Consistent with the notion that HSCs and ECs are derived from a common precursor, our findings suggest that under appropriate conditions, a subpopulation of $MB^{CD34+}$ or $MB^{Flk1-}$ can differentiate into ECs in vitro. Moreover, the in vivo results suggest that circulating $MB^{CD34+}$ or $MB^{Flk1+}$ in the peripheral blood may constitute a contingency source of ECs for angiogenesis. Incorporation of in situ differentiating EC progenitors into the neovasculature of these adult species is consistent with vasculogenesis, a paradigm otherwise restricted to embryogenesis (2,3). The fact that these cells do not incorporate into mature blood vessels not undergoing angiogenesis suggests that injury, ischemia, and/or active angiogenesis are required to induce in situ differentiation of $MB^{CD34+}$ to ECs.

Example II
EC Progenitors Augment Reendothelialization

Figure 9:
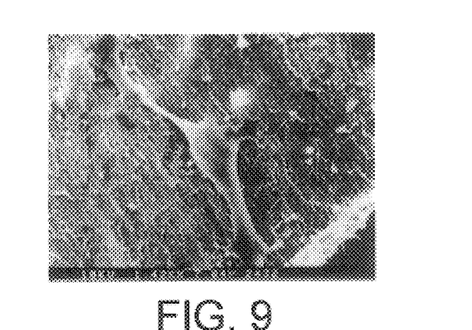
FIG. 9 is a photograph from a scanning electron microscope showing that EC progenitors had adhered to the denuded arterial surface and assumed a morphology suggestive of endothelial cells.

Following balloon injury, a denuded rat carotid artery was immediately excised and placed in culture in HUVEC medium, and DiI labeled CD34+EC progenitor cells were seeded onto the artery. After 1 wk, the artery was washed with PBS to remove non-adherent cells. Consistent with the ability of CD34+ cells to differentiate into filtrating cells, DiI labeled cells were found within the smooth muscle cell layer of the artery. Scanning electron microscopy of the intimal surface, however, showed that DiI-labeled cells also had adhered to the denuded arterial surface, assuming a morphology suggestive of ECs (FIG. 9). DiI labeled cells also incorporated into the capillary-like sprouts at the bare ends of the excised arterial segment, suggesting that CD34+ cells may be capable of participating in angiogenesis as well.

To determine if exogenously administered CD34+ EC progenitor cells can contribute to reendothelializationr of a denuded arterial surface in vivo, freshly isolated human CD34+ or CD34- cells were DiI labeled and seeded onto a denuded carotid artery of a nude rat. Following balloon denudation, $1.0 \times 10^6$ labeled cells in PBS was introduced into the denuded artery via a 22 G catheter, which remained in the artery for 30 min before the needle was withdrawn. The external carotid artery was then ligated, the common and internal carotid arterial ligatures removed, and the incision closed. The next day the rat was anesthetized and the vasculature perfusion fixed with Histo Choice (Amresco). The denuded arterial segment was excised and examined for the presence of adherent DiI labeled cells, which were identified in arteries seeded with CD34+ cells, but not CD34- cells.

The following references are cited throughout the specification. All documents mentioned herein are incorporated herein by reference.

(1) J. Folkman, Y. Shing, *J. Biol. Chem.* 267, 10931 (1992); W. Schaper, M. D. Brahander, P. Lewi, Circ. Res. 28, 671 (1971); W. Risau, *FASEB J.* 9, 926 (1995).

(2) W. Risau, H. Sariola, H-G. Zerwes, J. Sasse, P. Ekblom, et al, *Development* 102, 471 (1988); L. Pardanaud, C. Altman, P. Kitos, F. Dieterien-Lievre, *Development* 105, 473 (1989).

(3) I. Flamme, W. Risau, *Development* 116, 435 (1992).

(4) W. His, Abhandl. K. S. Ges. *Wiss. Math. Phys.* 22, 171 (1900); M. Weiss, S. H. Orkin, *J. Clin. Invest.* 97, 591 (1996).

(5) W. Brugger, S. Heimfeld, R. J. Berenson, R. Mertelsmann, L. Kanz, *N. Engl J. Med.* 333, 283 (1995); A. Kessinger, J. O. Armitage, Blood 77, 211 (1991); W. P. Sheridan, C. G. Begley, C. Juttener, *Lancet* 339, 640 (1992); E. J. Shpall, R. B. Jones, S. I. Bearman, *J. Clin. Oncol.* 12, 28 (1994).

(6) C. I. Civin, L. C. Strauss, C. Brovall, M. J. Frackler, J. F. Schwartz, et al, *J Immunol* 133, 157 (1984); F. Katz, R. W. Tindle, D. R. Sutherland, M. D. Greaves, *Leuk. Res.* 9, 191 (1985); R. G. Andrews, J. W. Singer, I. D. Bernstein, *Blood* 67, 842 (1986).

(7) J. Fina, H. V. Molgard, D. Robertson, N. J. Bradley, P. D. Managhan, et al, *Blood* 75, 2417 (1990); D. Soligo, D. Delia, A. Oriani, G. Cattoretti, A. Orazi, et al, *Leukemia* 5, 1026 (1991); A. Ito, S. Nomura, S. Hirota, T. Suda, Y. Kitamura, *Lab. Invest.* 72, 532 (1995).

(8) C. deVries, J. A. Escobedo, H. Ueno, K. Houck, N. Ferrara, et al, *Science* 255, 989 (1992); B. I. Terman, M. Dougher-Vermazen, M. E. Carrion, D. Dimitrov, D. C. Armellino, et al, *Biochem. Biophys. Res. Commun.* 187, 1579 (1992); F. Shalaby, J. Rossant, T. P. Yamaguchi, M. Gertsenstein, X-F. Wu, et al, *Nature* 376, 62 (1995).

(9) W. Matthews, C. T. Jordan, M. Gavin, N. A. Jenkins, N. G. Copeland, et al, *Proc. Natl. Acad. Sci. USA*. 88, 9026 (1991); B. Millauer, S. Wizigmann-Voos, H. Schnurch, R. Martinez, N. P. H. Moller, et al, *Cell* 72, 835 (1993); T. P. Yamaguchi, D. J. Dumont, R. A. Conlon, M. L. Breitman, J. Rossant, *Development* 118, 489 (1993).

(13) J. C. Voyta, D. P. Via, C. E. Butterfield, B. R. Zetter, *J. Cell Biol.* 99, 2034 (1984).

(14) B. Millauer, S. Wizigmann-Voos, H. Schnurch, R. Martinez, N. P. H. Moller, et al, *Cell* 72, 835 (1993); T. P. Yamaguchi, D. J. Dumont, R. A. Conlon, M. L. Breitman, J. Rossant, *Development* 118, 489 (1993); M. Miettinen, H. Holthofer, V. P. Lehto, A. Miettinen, I. Virtanen, *Am. J. Clin. Pathol.* 79, 32 (1983); E. A. Jaffe, R. L. Nachman, C. G. Becker, C. R. Minick, *J. Clin. Invest.* 52, 2745 (1973); P. J. Newman, M. C. Berndt, J. Gorski, G. C. White, S. Lyman, et al, *Science* 247, 1219 (1990); A. Vecchi, C. Garlanda, M. G. Lampugnani, M. Resnati, C. Matteucci, et al, *Eur. J. Cell Biol.* 63, 247 (1994); T. N. Sato, Y. Tozawa, U. Deutsch, K.

Wolburg-Buchholz, Y. Fujiwara, et al, *Nature* 376, 70 (1995); H. Schnurch, W. Risau, *Development* 119, 957 (1993); M. P. Bevilacqua, *Annu. Rev. Immuno.* 11, 767 (1993).

(15) S. P. Janssens, A. Shimouchi, T. Quertermous, D. B. Block, K. D. Bloch, *J. Biol. Chem.* 267, 14519 (1992); S. Lamos, P. A. Marsden, G. K. Li, P. Tempst, T. Michel, *Proc. Natl. Acad. Sci. USA* 89, 6348 (1992).

(16) R. van der Zee, F. Zoliman, J. Passeri, C. Lekutat, M. Silver, et al, *Circulation*, in press.

(17) K. Shibuki, D. Okada, *Nature* 358, 676 (1991).

(18) A. S. Weyrich, X-I. Ma, M. Buerke, T. Murohara, V. E. Armstead, et al, *Circ. Res.* 75, 692 (1994).

(19) B. Torok-Storb, *Blood* 72, 373 (1988); N. Dainiak, *Blood* 78, 264 (1991).

(20) J. Folkman, M. Klagsbrun, *Science* 235, 442 (1987); R. O. Hynes, *Cell* 48, 549 (1987); P. C. Brooks, R. A. F. Clark, D. A. Cheresh, *Science* 264, 569 (1994); M. Friedlander, P. C. Brooks, R. W. Shaffer, C. M. Kincaid, J. A. Varner, et al, *Science* 270, 1500 (1995).

(21) P. J. Simmons, B. Masinovdky, B. M. Longenecker, R. Berenson, B. Torok-Storb, et al, *Blood* 80, 388 (1992); J. L. Liesveld, K. E. Frediani, A. W. Harbol, J. F. DiPersio, C. N. Abboud, *Leukemia* 8, 2111 (1994).

(23) S. Takeshita, L. P. Zheng, E. Brogi, M. Kearney, L. Q. Pu, et al, *J. Clin. Invest.* 93, 662 (1994); L. Q. Pu, A. D. Sniderman, R. Brassard, K. J. Lachapelle, A. M. Graham, et al, *Circulation* 88, 208 (1993); R. Baffour, J. Berman, J. L. Garb, S. W. Rhee, J. Kaufman, et al, *J. Vasc. Surg.* 16, 181 (1992).

(24) J. M. Isner, A. Pieczek, R. Schainfeld, R. Blair, L. Haley, et al, *Lancet* 348, 370 (1996).

(25) P. A. D'Amore, R. W. Thompson, *Annu. Rev. Physiol.* 49, 453 (1987).

(26) M. R. Tschudi, M. Barton, N. A. Bersinger, P. Moreau, F. Cosentino, et al, *J. Clin. Invest.* 98, 899 (1996).

(27) Y. Sato, K. Okamura, A. Morimoto, R. Hamanaka, K. Hamanaguchi, et al, *Exp. Cell Res.* 204, 223 (1993); M. S. Pepper, N. Ferrara, L. Orci, R. Montesano, Biochem Biophys Res *Comm* 181, 902 (1991); D. R. Senger, S. R. Ledbetter, K. P. Claffey, A. Papadopoulos-Sergiou, C. A. Perruzzi, et al, *Am. J. PathoL* 149, 293 (1996).

This invention has been described in detail including the preferred embodiments thereof. However, it will be appreciated that those skilled in the art, upon consideration of this disclosure, may make modifications and improvements thereon without departing from the spirit and scope of the invention as set forth in the claims.

What is claimed is:

1. A pharmaceutical product comprising a nucleic acid encoding an endothelial cell mitogen and endothelial cell (EC) progenitors, in a physiologically acceptable administrable form, wherein the EC progenitors are CD34+, Flk-1+, and tie-2+.

2. The pharmaceutical product of claim 1, wherein the nucleic acid comprises a vector.

3. The pharmaceutical product of claim 2, wherein the vector comprises sequence from a DNA or RNA virus.

4. The pharmaceutical product of claim 3, wherein the vector is a retroviral vector.

5. The pharmaceutical product of claim 4, wherein the retroviral vector comprises sequence from moloney murine leukemia virus or human immunodeficiency (HIV) virus.

6. The pharmaceutical product of claim 5, wherein the vector comprises human immunodeficiency virus (HIV) gag and pol genes.

7. The pharmaceutical product of claim 6, the product further comprising another vector comprising sequence from the human immunodeficiency (HIV) env gene.

8. The pharmaceutical product of claim 2, wherein the vector comprises sequence from a DNA virus.

9. The pharmaceutical product of claim 8, wherein the vector comprises sequence from at least one of pox virus, herpes virus, adenovirus, or adeno-associated virus.

10. The pharmaceutical product of claim 9, wherein the vector is replication defective.

11. The pharmaceutical product of claim 9, wherein the pox virus is orthopox or avipox.

12. The pharmaceutical product of claim 9, wherein the herpes virus is herpes simplex I virus (HSV).

13. The pharmaceutical product of claim 1, wherein the nucleic acid further comprises an operably linked promoter.

14. The pharmaceutical product of claim 13, wherein the promoter is a cytomegalovirus (CMV), Rous sarcoma virus (RSV), MMT promoter, or a native promoter.

15. The pharmaceutical product of claim 13, wherein the nucleic acid further comprises at least one enhancer.

16. The pharmaceutical product of claim 15, wherein the enhancer is a tat gene or tar element.

17. The pharmaceutical product of claim 2, wherein the vector comprises sequence encoding a selectable marker.

18. The pharmaceutical product of claim 1, wherein the encoded endothelial cell mitogen is sufficient to stimulate at least one of native EC cells to proliferate, migrate, remodel or form new sprouts from parental vessels.

19. The pharmaceutical product of claim 18, wherein the encoded endothelial cell mitogen comprises a secretory signal sequence.

20. The pharmaceutical product of claim 1, wherein the EC progenitors are angioblasts.

21. The pharmaceutical product of claim 1, wherein the EC progenitors are detectably-labeled.

22. The pharmaceutical product of 21, wherein the detectably-labeled EC progenitors are radiolabeled.

23. The pharmaceutical product of claim 1, wherein the EC progenitors are obtained from human mononuclear cells, heterologous or autologous umbilical cord blood, or peripheral blood.

24. The pharmaceutical product of claim 23, wherein the EC progenitors are obtained from the leukocyte fraction of peripheral blood.

* * * * *